(12) United States Patent
Garlichs et al.

(10) Patent No.: US 8,907,119 B2
(45) Date of Patent: Dec. 9, 2014

(54) PROCESS FOR PREPARING MERCAPTOALKYL CARBOXYLATES

(75) Inventors: Florian Garlichs, Neustadt (DE); Jens Baldamus, Ludwigshafen (DE); Gerd Kaibel, Lampertheim (DE)

(73) Assignee: BASF SE, Ludwigshafen (DE)

( * ) Notice: Subject to any disclaimer, the term of this patent is extended or adjusted under 35 U.S.C. 154(b) by 230 days.

(21) Appl. No.: 13/591,398

(22) Filed: Aug. 22, 2012

(65) Prior Publication Data

US 2013/0217912 A1   Aug. 22, 2013

Related U.S. Application Data

(60) Provisional application No. 61/526,714, filed on Aug. 24, 2011.

(30) Foreign Application Priority Data

Aug. 24, 2011   (EP) ................................ 11178664

(51) Int. Cl.
*C07C 319/12*   (2006.01)
*C07C 319/22*   (2006.01)

(52) U.S. Cl.
CPC ............ *C07C 319/12* (2013.01); *C07C 319/22* (2013.01)
USPC ........................................................ 560/147

(58) Field of Classification Search
CPC .................................................... C07C 319/12
USPC ........................................................ 560/147
See application file for complete search history.

(56) References Cited

U.S. PATENT DOCUMENTS

| | | | |
|---|---|---|---|
| 4,615,836 A | 10/1986 | Bobsein | |
| 5,916,987 A | 6/1999 | Kobayashi et al. | |
| 2008/0132621 A1 | 6/2008 | Krainer et al. | |
| 2010/0298589 A1 | 11/2010 | Krainer et al. | |

FOREIGN PATENT DOCUMENTS

| | | |
|---|---|---|
| WO | WO 2008/069904 A1 | 6/2008 |
| WO | WO 2010/094641 A1 | 8/2010 |

OTHER PUBLICATIONS

European Search Report issued Mar. 27, 2012 in corresponding European Application No. 11 17 8664 filed on Aug. 24, 2011 (with an English Translation of Categories).
Hartmut Seliger et al., "Synthesis of Aliphatic Sulfenyl Halides Containing Ester Groups", Synthetic Communications, vol. 10, No. 3, 1980, pp. 175-182.
J. W. John Bosco et al., "Potassium Fluoride Assisted Selective Acetylation of Alcohols with Acetic Acid", Synthetic Communications, vol. 34, No. 15, 2004, pp. 2849-2855.
Moshe Nahmany et al., "One-Step Tethering of ω-Mercaptoalkyl Function to Alcohols", Synthesis, No. 17, 2006, pp. 2841-2844.
Habib Firouzabadi et al., "Solid trichlorotitanium(IV) trifluoromethanesulfonate $TiCl_3$ (OTf) catalyzed efficient acylation of -OH and -SH: Direct esterification of alcohols with carboxylic acids and transesterification of alcohols with esters under neat conditions", Journal of Molecular Catalysis A: Chemical, vol. 289, 2008, pp. 61-68.
Reza Tayebee et al., "Acetylation of Alcohols Catalyzed by Dodecatungsto(molybdo)phosphoric acid", Monatshefte für Chemie, vol. 137, 2006, pp. 1063-1069.
Rajesh K. Pandey et al., "Synthesis of ceria-yttria based strong Lewis acid heterogeneous catalyst: Application for chemoselective acylation and ene reaction", Journal of Molecular Catalysis A: Chemical, vol. 245, 2006, pp. 255-259.
Pradeep Kumar et al., "Yttria-Zirconia Based Lewis Acid: An Efficient and Chemoselective Catalyst for Acylation Reactions", Synlett, No. 2, 2001, pp. 206-209.
International Search Report Issued Nov. 21, 2012 in PCT/EP2012/065862 (with English translation of Categories of Cited Documents).

*Primary Examiner* — Yong Chu
(74) *Attorney, Agent, or Firm* — Oblon, Spivak, McClelland, Maier & Neustadt, L.L.P.

(57) ABSTRACT

In the acid-catalyzed esterification of mercaptoalkyl alcohols by means of carboxylic acids to form mercaptoalkly carboxylates, formation of undesirable, usually sparingly soluble byproducts usually occurs. The process of the invention in the absence of acid catalysts avoids the formation of such byproducts. Particularly when the esterification of the invention is carried out as reactive distillation using reactive column and residence vessel, good degrees of conversion can also be obtained without acid catalyst and at the same time the formation of the by-products can be largely avoided.

10 Claims, 1 Drawing Sheet

PROCESS FOR PREPARING MERCAPTOALKYL CARBOXYLATES

The present application incorporates by reference the prior U.S. application 61/526,714 filed on Aug. 24, 2011.

The invention relates to a process for preparing mercaptoalkyl carboxylates by autocatalytic reaction of carboxylic acids with mercaptoalkyl alcohols.

The industrially most important method of preparing carboxylic esters is direct esterification of a carboxylic acid by means of an alcohol. The carboxylic acids used react only very slowly because of the low acidity. The addition of strong acids (for example sulfuric acid, p-toluene-sulfonic acid, acidic ion exchangers and titanium alkoxylates) as catalyst for the esterification is therefore prior art. The esterification is an equilibrium reaction. To shift the reaction equilibrium to the side of the reaction products, it is therefore usual either to initially charge the starting materials in excess or to remove the products from the reaction mixture during the reaction. Thus, for example, the water of reaction is removed in gaseous form from the reaction mixture in order to shift the equilibrium in the esterification to the side of the ester. This is frequently achieved using an entrainer.

In azeotropic distillation, the starting materials, carboxylic acid and alcohol, are usually placed in the reaction vessel together with entrainer and catalyst. The water of reaction is then removed by distillation together with the entrainer, usually with recirculation of the entrainer, until a satisfactory reaction conversion has been achieved and the ester can be isolated from the reaction mixture.

In the case of reactive distillations, the carboxylic acid is usually reacted with the alcohol in a reaction zone provided with catalyst. The products formed (water of reaction and carboxylic ester) are then separated off as overhead products or as bottom products from the column.

Carboxylic esters can generally also be prepared by transesterification or reaction of the alcohol with activated carboxylic acid derivatives (for example acid chlorides or acid anhydrides). This is employed especially in the reaction of thermally sensitive substrates or in the preparation of sensitive products. However, esterification processes starting out from activated carboxylic acid derivatives are usually costly and uneconomical.

Esters of carboxylic acids and mercaptoalkyl alcohols, viz. mercaptoalkyl carboxylates, in particular mercaptoethyl propionate, are suitable for use as molar mass regulators in polymerization reactions instead of otherwise customary but environmentally unfriendly long-chain mercaptans (WO 2010/094641).

However, in the homogeneously acid-catalyzed esterification of carboxylic acids by means of mercaptoalkyl alcohols (acid-catalyzed azeotropic esterification) in a batch process, for example using p-toluenesulfonic acid (U.S. Pat. No. 5,916,987) as homogeneous catalyst, there is increased formation of undesirable high boilers (oligomers or polymers of the mercaptoalkyl alcohol and/or O,S-acylated compounds). To avoid the formation of these by-products, the reaction has to be carried out at high dilution. This in turn increases the outlay in the preparation of the ester, since the solvent added has to be removed in a complicated fashion by distillation after the reaction. In addition, a complicated removal of the catalyst is necessary in the case of homogeneously catalyzed esterification. WO 2008/069904 describes the acid-catalyzed preparation of a mercaptoalkyl carboxylate starting from an acid anhydride as activated carboxylic acid derivative. Seliger and Görtz (Synthetic Communications (1980), 10: 175-182) describe the azeotropic esterification of specific carboxylic acids with specific mercaptoalkyl alcohols even without addition of catalyst. Barco et al. (Synthetic Organic Chemistry (2004), 34; 2849-2855) describe such an azeotropic esterification in the presence of calcium fluoride as catalyst. In the case of Nahmany and Melman (Synthesis, (2006), 17, 2841-2844) the esterification is achieved on the other hand by addition of dicydohexycarbodiimide.

Processes in which the esterification reaction is homogeneously catalyzed (Firouzabadi et al., J Molecular Catalysis A: Chemical (2008), 289:61-68; Tayebee et al., Monatshefte Chemie (2006), 137:1063-1069; Pandey et al., J Molecular Catalysis A: Chemical (2006), 245:255-259; Kumar et al., Synlett (2001), 2:206-209, U.S. Pat No. 4,615,836) have also been described for the preparation of mercaptoalkyl carboxylates. When an acidic heterogeneous catalyst is used, the separation of the catalyst from the product mixture is significantly simpler and less complicated than when homogeneous acid catalysts are used. However, the use of activated carboxylic acid derivatives, e.g. carboxylic anhydrides, is usually necessary or large amounts of the catalyst or large excesses of acid are necessary. However, undesirable by-products such as oligomers or polymers of the mercaptoalkyl alcohol and/or O,S-acylated compounds are also formed in the heterogeneously acid-catalyzed esterification. The esters obtained in this way therefore usually have to be purified by distillation. The by-products are sometimes obtained in the form of solids, which is particularly disadvantageous from a process engineering point of view.

The object of the invention can therefore be considered that of preparing mercaptoalkyl carboxylates by esterification of carboxylic acids by means of mercaptoalkyl alcohols while avoiding the disadvantages of the prior art, in particular the formation of undesirable by-products as is observed in homogeneously or heterogeneously acid-catalyzed esterifications. This object is achieved by the embodiments claimed and described in the following.

The present invention accordingly provides a process for preparing mercaptoalkyl carboxylates by autocatalytic esterification of carboxylic acids by means of mercaptoalkyl alcohols by reactive distillation in the absence of an additional active acid catalyst (homogeneous or heterogeneous).

An additional active acid catalyst (homogeneous or heterogeneous) for the purposes of the invention is an acid (Lewis or Brønsted acid) which is not identical to the carboxylic acid to be esterified and brings about, under the given esterification conditions and in the amount added or in the proportion added averaged over the total esterification mixture, an increase in the rate of the esterification of the carboxylic acid by means of the mercaptoalkyl alcohol by at least 50%, by at least 100% or by at least 200%, compared to the otherwise identical esterification mixture without addition of an acid (in addition to the carboxylic acid to be esterified). The esterification conditions are, in particular, characterized by the type and amount or the proportion of the starting materials, carboxylic acid and mercaptoalkyl alcohol used, the temperature and the pressure and the type and amount or the proportion of an optional solvent used. The rate of the esterification is the limit of the rate of formation of the esterification product, viz. mercaptoalkyl carboxylate, at the beginning of the reaction. It can be determined as the gradient of the tangents in the measurement of the ester concentration versus time at the time of commencement of the esterification reaction. The rate of the esterification is thus the derivative with respect to time of the function of ester concentration versus time at the time of commencement of the esterification. For the purposes of the invention, absence of additional active acid catalyst (homogeneous or heterogeneous) is then the case when, although an additional acid has been added to the reaction mixture, this does not bring about an increase in the esterification rate to the abovementioned degree under the reaction conditions, or is added in an amount or proportion which is too small to bring about such an increase in the esterification rate.

The invention therefore provides, in particular, a process for preparing mercaptoalkyl carboxylates by esterification from the starting materials carboxylic acid and mercaptoalkyl alcohol, wherein the esterification is carried out in the absence of an additional active acid catalyst, where said additional active acid catalyst is an amount of an acid which brings about an increase in the rate of said esterification, averaged over the total esterification mixture, by at least 50%, by at least 100% or by at least 200%, under otherwise identical esterification conditions, compared to the esterification of the carboxylic acid by means of the mercaptoalkyl alcohol without additional acid, where the esterification is carried out as reactive distillation in which a) the starting materials carboxylic acid and mercaptoalkyl alcohol are fed as a continuous stream into the reaction zone of a rectification column,
b) the starting materials react in the rectification column to form the reaction products mercaptoalkyl carboxylate and water of reaction,
c) the reaction mixture is fractionally distilled in the rectification column and
d) a mercaptoalkyl carboxylate-comprising fraction is discharged at the bottom and a fraction comprising water of reaction is discharged at the top of the rectification column.

The amount or proportion of mercaptoalkyl carboxylate formed during the course of the esterification reaction can be determined by means of GC or HPLC analysis, in particular using internal or external standards, for the starting materials and products of the esterification reaction.

In principle an esterification can be carried out discontinuously (batch process) as azeotropic distillation. The process of the invention is carried out as a reactive distillation. In this case, the starting materials, viz. mercaptoalkyl alcohol and carboxylic acid, are usually fed continuously into a column (rectification column with reaction zone) in an essentially stoichiometric ratio of, for example, from 0.8 to 1.2 for molar amount of mercaptoalkyl alcohol to molar amount of carboxylic acid. The water of reaction formed is separated off at the top and the mercaptoalkyl carboxylate formed is taken off at the bottom. Carrying out the process as a reactive distillation, continuously with continuous removal of the water of reaction and the reaction product, makes advantageous total conversions for the reaction possible.

The process of the invention for preparing mercaptoalkyl carboxylates is thus, in a preferred embodiment, carried out as reactive distillation in which a) the starting materials carboxylic acid and mercaptoalkyl alcohol are fed as a continuous stream into the reaction zone of a rectification column,
b) the starting materials react in the rectification column to form the reaction products mercaptoalkyl carboxylate and water of reaction,
c) the reaction mixture is fractionally distilled in the rectification column and
d) a mercaptoalkyl carboxylate-comprising fraction is discharged at the bottom and a fraction comprising water of reaction is discharged at the top of the rectification column.

All steps of the process are preferably carried out continuously.

In one embodiment of the invention, the esterification is carried out to partial conversion in a residence vessel. The residence time is preferably selected so that the initially fast reaction rate of the equilibrium reaction is covered. The residence time is preferably set so that under the given reaction conditions (in particular at the temperature set and for the starting material selected) from 5 to 50%, preferably from 10 to 30%, particularly preferably from 15 to 25%, of the equilibrium concentration of the ester is formed. The residence time is given as the quotient of the volume of the total reaction space divided by the total flow rate of the streams fed into the total reaction space, i.e. the freshly introduced carboxylic acid and the freshly introduced mercaptoalkyl alcohol and any additional solvent and/or entrainer fed in. The total reaction space is the reaction space of the apparatus in which the starting materials can esterify to form the product; it is formed by the reaction space of the residence vessel and the reaction zone of the rectification column and also the connecting lines between residence vessel and rectification column. The reaction space of the residence vessel usually makes up the predominant part of the total reaction space, preferably at least 60%, particularly preferably at least 80%, in particular at least 90%. The residence time can therefore usually be determined very well as quotient of the volume of the reaction space of the residence vessel divided by the total flow rate of the streams fed into the total reaction space. The residence time can thus be set, in particular, via the ratio of the dimensions of the residence vessel to the desired throughput. The residence vessel preferably has a stirrer, a pump circuit and/or a temperature control facility.

The reaction in the residence vessel is preferably carried out at a temperature of from 80 to 200° C., particularly preferably from 100 to 160° C., in particular from 100 to 140° C. The absolute pressure in the residence vessel is preferably from 0.5 to 16 bar, particularly preferably from 0.9 to 6 bar. The pressure in the residence vessel is at least equal to the vapor pressure of the reaction mixture at the selected temperature. The temperature in the residence vessel is preferably selected so that it corresponds to or is slightly higher than the temperature at the inlet to the column but corresponds to not more than the temperature at the bottom of the column. The reaction space of the residence vessel is in volume exchange with the reaction zone of a rectification column having a stripping section and enrichment section. In the rectification column the products are separated off at the top or the bottom. A product-depleted stream is obtained as side offtake stream from the column. In a preferred variant, this stream is recirculated to the residence vessel. The use of a residence vessel when carrying out the reactive distillation according to the invention makes it possible to subject comparatively large amounts of starting material to the esterification reaction, while the removal of the products (ester and water of reaction) can be carried out in a rectification column which is comparatively small for the given throughput and is thus advantageous. The use of the residence vessel results in the appropriate residence time not having to be realized in the reaction zone of the rectification column, as a result of which the rectification column can be made comparatively small.

In a preferred embodiment, the process of the invention for preparing mercaptoalkyl carboxylate is thus carried out as reactive distillation in combination with a residence vessel, in which a) the starting materials, viz. carboxylic acid and mercaptoalkyl alcohol, are fed as continuous streams to the overall reaction space, comprising the reaction space of the residence vessel and the reaction zone of the rectification column, b) the starting materials react in the overall reaction space so as to convert them partly into mercaptoalkyl carboxylate and water of reaction, c) the reaction mixture from step b) comprising mercaptoalkyl carboxylate and water of reaction as products of the esterification and also unreacted starting materials is fed from the residence vessel to the rectification column, d) the mercaptoalkyl carboxylate and the water of reaction are separated off by distillation from the reaction mixture in the rectification column and are discharged at the bottom or at the top of the rectification column while product-depleted reaction mixture is discharged as side offtake stream from the rectification column and e) the product-depleted reaction mixture discharged as side offtake stream from the rectification column in step d) is recirculated to the residence vessel.

Here, one or more product-depleted fractions can be discharged as side offtake stream or streams from the rectification column, depending on the respective boiling points of the starting materials and products under the distillation conditions. Preference is given to carrying out all steps of the process continuously. In particular, the introduction of the reaction mixture from the residence vessel into the rectification column (step c) and the recirculation of the product-depleted fraction or product-depleted fractions as side offtake stream or streams from the rectification column to the residence vessel (step e) are effected as continuous streams. The fractional distillation in the rectification column is preferably carried out under reduced pressure, for example at an absolute pressure of from 1 to 800 mbar, typically at an absolute pressure of from 10 to 500 mbar. Under such conditions, the distillation can be carried out at a lower temperature at the bottom, by means of which the formation of undesirable by-products can be additionally reduced. However, the fractional distillation can also be carried out at atmospheric pressure or superatmospheric pressure.

Depending on the choice of the starting materials, the water of reaction to be taken off at the top of the column can carry azeotropically bound starting material with it. In a preferred variant, the overhead product from the column is in such cases mixed with a suitable auxiliary (e.g. cyclohexane, toluene) and fed to a phase separation vessel so that the mixture separates into a liquid upper phase comprising predominantly auxiliary and starting material and a lower phase comprising predominantly water. The water phase is discharged, and the auxiliary/starting material phase is recirculated to the top of the column.

The esterification process of the invention is carried out using, for example, branched or unbranched carboxylic acids having from 2 to 8 carbon atoms, preferably from 2 to 5 carbon atoms. Suitable carboxylic acids are, for example, acetic acid, propionic acid, butyric acid, isobutyric acid, valeric acid, isovaleric acid, caproic acid, enanthic acid or caprylic acid.

Furthermore, the esterification process of the invention is carried out using, for example, branched or unbranched mercaptoalkyl alcohols having from 2 to 4 carbon atoms. Suitable mercaptoalkyl alcohols are, for example, 2-mercaptoethanol, 2-mercaptopropanol, 3-mercapto-propanol, 1-mercapto-2-propanol, 2-mercaptobutanol, 3-mercaptobutanol, 4-mercaptobutanol, 1-mercapto-2-butanol, 1-mercapto-3-butanol, 2-mercapto-3-butanol or mercaptoisobutanol.

In the esterification of carboxylic acids having from 2 to 8 carbon atoms, in particular carboxylic acids having from 2 to 5 carbon atoms, by means of mercaptoalkyl alcohols having from 2 to 4 carbon atoms in a reactive distillation, the products formed (ester and water of reaction) can be separated off advantageously from the unreacted starting materials (mercaptoalkyl alcohol and carboxylic acid) because of the different boiling points of water of reaction, starting materials and ester.

A preferred embodiment of the process of the invention provides the esterification of propionic acid by means of 2-mercaptoethanol to form mercaptoethyl propionate.

The esterification according to the invention of carboxylic acid by means of mercaptoalkyl alcohol is preferably carried out at a temperature of from 80 to 200° C., preferably from 100 to 160° C., in particular from 100 to 140° C., and at an absolute pressure of from 0.5 to 16 bar, preferably from 0.9 to 6 bar.

The esterification according to the invention of carboxylic acid by means of mercaptoalkyl alcohols can be carried out in the presence of entrainers. For the purposes of the invention, entrainers do not include any acids. Preferred entrainers are aromatic and/or aliphatic hydrocarbons such as toluene, xylene, cyclohexane and/or cycloheptane, in particular toluene. In this case, the esterification of the invention is preferably carried out in the presence of not more than 5% by weight of entrainer, based on the total amount of the starting materials (carboxylic acid and mercaptoalkyl alcohol). The esterification of the invention can also be carried out in the presence of solvents. For the purposes of the invention, solvents do not include any acids. Solvents can also act as entrainers and vice versa. In this case the esterification of the invention is preferably carried out in the presence of not more than 5% by weight of solvent and/or entrainer, based on the total amount of the starting materials (carboxylic acid and mercaptoalkyl alcohol). In one embodiment, the esterification of the invention is carried out as a reactive distillation without addition of solvent and/or entrainer.

It has been observed that the formation of undesirable by-products was able to be significantly reduced in the esterification according to the invention of mercaptoalkyl alcohols by means of carboxylic acids without additional active acid catalyst (homogeneous or heterogeneous). The by-products are, in particular, O,S-acylated or oligomeric compounds of the mercaptoalkyl alcohol. Since these by-products generally precipitate as insoluble solids, they are particularly problematical for carrying out the process in industry. The reduction in reaction rate associated with not adding active acid catalysts can be compensated according to the invention by carrying out the esterification by means of reactive distillation, in particular with use of a residence vessel for the reaction. Even when the reaction temperature and the reaction time (residence time) are increased, so as to achieve a conversion comparable to that obtained in a catalytic reaction of mercaptoalkyl alcohols with carboxylic acids, the formation of by-products observed in the catalytic reaction was avoided. The process of the invention offers an effective substitute for the catalytic esterification of mercaptoalkyl alcohols by means of carboxylic acids with avoidance or at least reduction of the by-product formation which otherwise occurs.

EXAMPLES

The invention will now be illustrated by the following, nonlimiting examples.

Example 1

Figure 2:
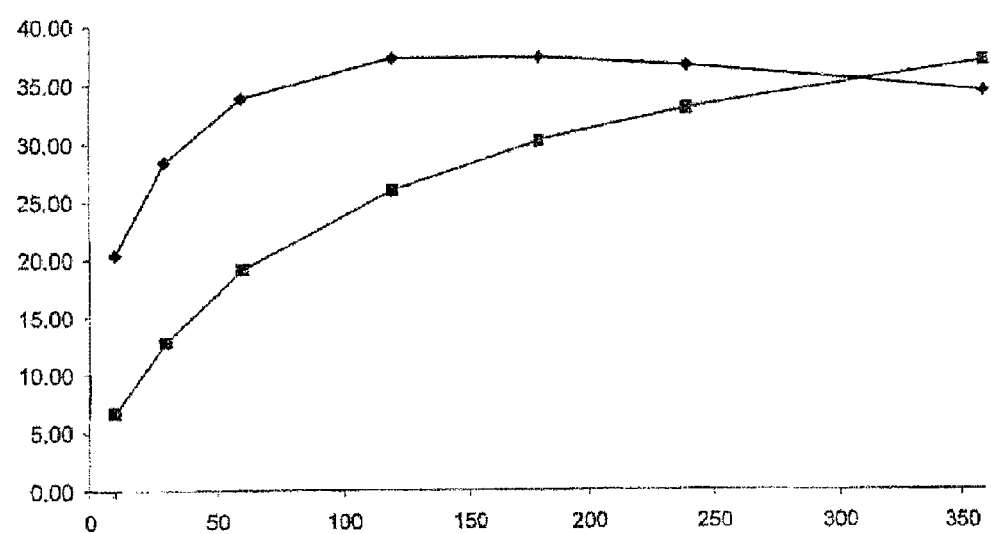
FIG. 2 shows the yield in the esterification of propionic acid by means of mercaptoethanol as a function of time. The proportion of mercaptoethyl propionate in % by weight (y axis) was measured by means of gas-chromatographic analysis (GC analysis) as a function of the reaction time in min (x axis). The yield in an esterification without addition of catalyst (ex. 1; -■-) and the yield in an esterification with addition of a heterogeneous acid catalyst (comparative ex. 1; -♦-) are shown as a function of time.

Esterification of Propionic Acid by Means of Mercaptoethanol Without Addition of Acid Catalyst and Without Entrainer In a 250 ml four-neck flask, 78.1 g of mercaptoethanol (1 mol) and 74.1 g of propionic acid (1 mol) were combined and heated to 140° C. The internal temperature during the reaction dropped to 120° C. as a result of the water of reaction formed. The yield of mercaptoethyl propionate during the course of the reaction was monitored by means of GC measurements during the reaction and is shown in FIG. 2. After 480 min, the reaction mixture was cooled. After cooling, the reaction mixture was a clear, colorless liquid. GC analysis of the crude product indicated a composition of 26.6% by weight of propionic acid (corresponding to 37.6 g), 30.2% by weight of mercaptoethanol (corresponding to 42.6 g), 37.1% by weight of mercaptoethyl propionate (corresponding to 52.3 g, 39.0% of the theoretical yield) and 0.64% by area of high boilers (% by area is percent by area of the peak in the GC chromatogram).

Comparative Example 1

Esterification of Propionic Acid by Means of Mercaptoethanol Without Entrainer but With Addition of a Heterogeneous Acid Catalyst In a 250 ml four-neck flask, 78.1 g of mercaptoethanol (1 mol) and 74.1 g of propionic acid (1 mol) were combined and 5% by weight of the heterogeneous catalyst Amberlyst® 15 (from Rohm and Haas Company) was added. The mixture was heated to 80° C. The yield of mercaptoethyl propionate over the course of the reaction was monitored by means of GC measurements during the reaction and is shown in FIG. 2. Oligomeric by-products which precipitated as solid were formed during the reaction. The formation of this solid is also the cause of the decrease in the ester yield after a reaction time of about 120 minutes, as can be seen in FIG. 2.

Although the addition of the heterogeneous acid catalyst significantly increases the reaction rate of the esterification compared to a batch without additional catalyst (Ex. 1), there is also increased formation of undesirable by-products (formation of solid).

Comparative Example 2

Esterification of Propionic Acid by Means of Mercaptoethanol in the Presence of an Acidic Catalyst and an Entrainer (Toluene)

The reaction mixtures A, B and C as indicated in Table 1 were placed in a 500 ml ground-flange reactor. The reaction mixture was in each case heated to reflux and the water of reaction formed is separated off on a phase separator (90 min at reflux in the case of variants A and B and 150 min at reflux in the case of variant C). In variants A and B, p-toluenesulfonic acid was used as homogeneous acid catalyst, while the heterogeneous gas catalyst Amberlyst 15 was used in variant C. In all three variants, the starting materials were diluted with a large amount of entrainer (toluene) (25% by weight based on the total amount of the starting materials in variant A and 150% by weight based on the total amount of the starting materials in the case variants B and C).

TABLE 1

|  | Reaction mixture A | Reaction mixture B | Reaction mixture C |
|---|---|---|---|
| Mercaptoethanol | 257.8 g (3.3 mol) | 117.2 g (1.5 mol) | 117.2 g (1.5 mol) |
| Propionic acid | 244.5 g (3.3 mol) | 111.1 g (1.5 mol) | 111.1 g (1.5 mol) |
| Acidic catalyst | p-toluenesulfonic acid | | Amberlyst 15 |
|  | 6.3 g (0.033 mol) | 2.9 g (0.015 mol) | 4.0 g |
| Toluene | 125.6 g | 342.5 g | 342.5 g |

After cooling, the reaction mixture of variants A and B was present as a clear, virtually colorless solution, but solid had formed in the case of variant A. In the case of variant C, the reaction mixture was present as a milky turbid solution with a proportion of white, amorphous solid after cooling. The interior of the apparatus was coated with a milky turbid film. The solid formed was sparingly soluble (solvents: acetone, water, DMSO, DCM) and could be removed from the apparatus only by mechanical means. The catalyst was visually unchanged.

GC analysis of the crude product of variant A indicated a composition of 5.9% by weight of propionic acid (corresponding to 39.3 g), 2.9% by weight of mercaptoethanol (corresponding to 16.2 g), 57.6% by weight of mercaptoethyl propionate (corresponding to 293.3 g, 72.6% of the theoretical yield) and 4.7% by area of high boilers. GC analysis of the crude product of variant B indicated a composition of 1.2% by weight of propionic acid (corresponding to 6.3 g), 0.9% by weight of mercaptoethanol (corresponding to 4.6 g), 32.2% by weight of mercaptoethyl propionate (corresponding to 170.1 g, 84.5% of the theoretical yield) and 0.84% by area of high boilers. GC analysis of the crude product of variant C indicated a composition of 14.8% by weight of propionic acid (corresponding to 75.6 g), 7.5% by weight of mercaptoethanol (corresponding to 39.7 g), 7.8% by weight of mercaptoethyl propionate (corresponding to 41.4 g, 20.6% of the theoretical yield). Owing to the massive formation of insoluble solids, a meaningful determination of the amount of high boilers was not possible.

Even when the starting materials were highly diluted with 25% by weight of toluene, it was not possible to avoid the formation of high-boiling by-products in the homogeneously acid-catalyzed esterification. Only at very high dilution of the starting materials with 150% by weight of toluene could the formation of high-boiling by-products be largely avoided in the homogeneously acid-catalyzed esterification (variant B). Nevertheless, even at such a high dilution with toluene, massive formation of undesirable insoluble by-products occurred in the case of the heterogeneously catalyzed esterification (variant C).

Dilution of the starting materials with entrainers allows the formation of undesirable by-products in the acid-catalyzed esterification of carboxylic acids by means of mercaptoalkyl alcohols to be avoided only when very high dilutions are set and only in the case of particular acid catalysts.

Example 2

Figure 1:
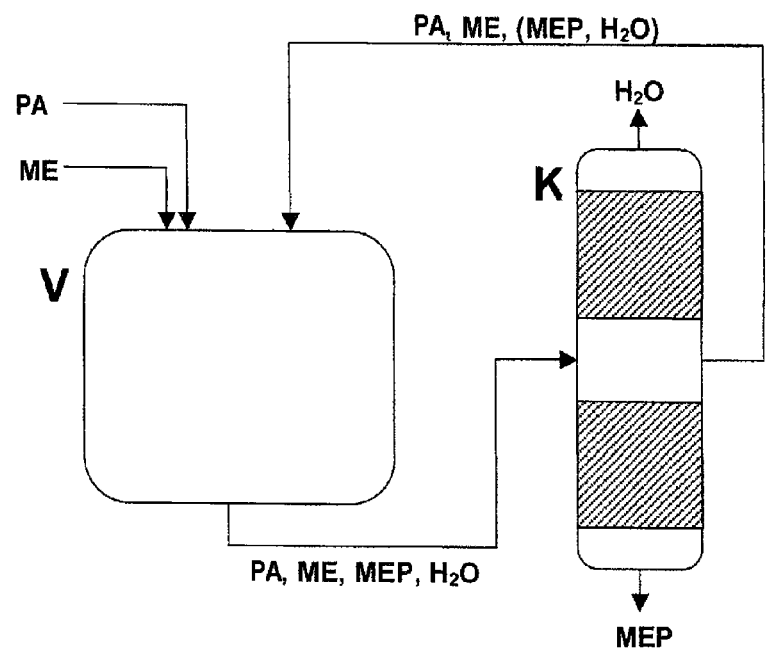
FIG. 1 illustrates the process of the invention for the example of a reactive distillation for the esterification of propionic acid (PA) by means of mercaptoethanol (ME) to form the ester mercaptoethyl propionate (MEP). The starting materials propionic acid (PA) and mercaptoethanol (ME) are introduced into the residence vessel (V). The residence vessel can be maintained at an esterification temperature and be equipped with a stirrer. In this vessel, the alcohol and the carboxylic acid react to give the ester with formation of water of reaction ($H_2O$). Depending on the residence time, the equilibrium concentration of the esterification products can be more or less fully attained. The residence time is derived from the inflow of the starting materials (including recirculated starting materials) and the volume of the residence vessel. The reaction mixture (PA, ME, MEP, $H_2O$) from the residence vessel (V) is then introduced into a column (K) for the reactive distillation. In the column (K), the components of the reaction mixture are separated. While the esterification product, viz. mercaptoethyl propionate (MEP), is separated off at the bottom and the water of reaction ($H_2O$) is separated off at the top, a product-depleted stream (PS, ME, (MEP, $H_2O$)) is taken off as side offtake stream from the column (K) and recirculated to the reaction mixture in the residence vessel (V). Carrying out the reactive distillation continuously with use of a residence vessel allows the disadvantage of the comparatively low reaction rate of the esterification reaction in the absence of an acid catalyst to be compensated.

Esterification of Propionic Acid by Means of Mercaptoethanol as Reactive Distillation With Residence Vessel and Without Addition of Acid Catalyst 25 g/h of propionic acid and 28 g/h of mercaptoethanol were fed into the residence vessel of a continuous laboratory plant (schematically shown in FIG. 1). The residence vessel (V) was externally heated ($T_V$=115° C.). The pressure at the top of the column (K) was 284 mbar. A temperature profile (bottom: 138° C. and top: 39° C.) was established over the column. The residence vessel had a fill level of from about 1 to 1.5 l. A stream of the reaction mixture amounting to from 0.15 to 0.40 l/h was conveyed from the residence vessel into the column. A reaction mixture depleted in esterification product, comprising unreacted starting materials (propionic acid and mercaptoethanol), was discharged as side offtake stream from the column and recirculated to the residence vessel. Water of reaction was separated off at the top of the column. The esterification product, viz. mercaptoethyl propionate, was obtained at the bottom of the column. The bottom output comprised over 90% by area of mercaptoethyl propionate according to GC analysis.

The invention claimed is:

1. A process for preparing a mercaptoalkyl carboxylate, the process comprising:
    esterifying carboxylic acid with mercaptoalkyl alcohol in absence of an additional active acid catalyst where the esterifying is carried out as reactive distillation;
    feeding the carboxylic acid and mercaptoalkyl alcohol as a continuous stream into a reaction zone of a rectification column;
    reacting the carboxylic acid and mercaptoalkyl alcohol in the rectification column to form a reaction product of mercaptoalkyl carboxylate and water of reaction;
    fractionally distilling the reaction product in the rectification column;
    discharging a fraction comprising the mercaptoalkyl carboxylate at a bottom of the rectification column; and
    discharging a fraction comprising the water of reaction at the top of the rectification column.

2. A process for preparing a mercaptoalkyl carboxylate, the process comprising:
    esterifying carboxylic acid with mercaptoalkyl alcohol in absence of an additional active acid catalyst, the esterifying being carrying out as reactive distillation in combination with a residence vessel;
    feeding viz. carboxylic acid and mercaptoalkyl alcohol as continuous streams to an overall reaction space, the overall reaction space comprising a reaction space of a residence vessel and a reaction zone of a rectification column;
    reacting the viz. carboxylic acid and mercaptoalkyl alcohol in the overall reaction space to partially convert them into mercaptoalkyl carboxylate and water of reaction;
    feeding a reaction mixture comprising an esterification product of mercaptoalkyl carboxylate and water of reaction, and unreacted viz. carboxylic acid and mercaptoalkyl alcohol from the residence vessel to the rectification column;
    separating off the mercaptoalkyl carboxylate and the water of reaction by distillation from the reaction mixture in the rectification column;
    discharging the mercaptoalkyl carboxylate at a top of the rectification column and the water of reaction at a bottom of the rectification column while a product-depleted reaction mixture is discharged as side offtake stream from the rectification column; and
    recirculating the product-depleted reaction mixture discharged as side offtake stream from the rectification column to the residence vessel.

3. The process according to claim 1,
    wherein the esterifying is carried out in presence of not more than 5% by weight of entrainer, based on a total amount of the carboxylic acid and mercaptoalkyl alcohol.

4. The process according to claim 1, wherein the esterifying is carried out at a temperature of from 80 to 200° C.

5. The process according to claim 1, wherein the carboxylic acid has from 2 to 8 carbon atoms and a single carboxylic acid group.

6. The process according to claim 1, wherein the mercaptoalkyl alcohol has from 2 to 4 carbon atoms, a single alcohol group, and a single thiol group.

7. The process according to claim 2,
    wherein the esterifying is carried out in presence of not more than 5% by weight of entrainer, based on a total amount of the carboxylic acid and mercaptoalkyl alcohol.

8. The process according to claim 2, wherein the esterifying is carried out at a temperature of from 80 to 200° C.

9. The process according to claim 2, wherein the carboxylic acid has from 2 to 8 carbon atoms, and a single carboxylic acid group.

10. The process according to claim 2, wherein the mercaptoalkyl alcohol has from 2 to 4 carbon atoms, a single alcohol group and a single thiol group.

* * * * *